(12) United States Patent
Vankoski et al.

(10) Patent No.: US 7,503,894 B2
(45) Date of Patent: Mar. 17, 2009

(54) LIT RETRACTOR

(75) Inventors: Stephen J. Vankoski, Fort Wayne, IN (US); Robert D. Krebs, Warsaw, IN (US); Richard Berger, Chicago, IL (US)

(73) Assignee: Zimmer Technology, Inc., Waraw, IN (US)

( * ) Notice: Subject to any disclaimer, the term of this patent is extended or adjusted under 35 U.S.C. 154(b) by 451 days.

(21) Appl. No.: 10/356,292

(22) Filed: Jan. 31, 2003

(65) Prior Publication Data

US 2004/0172105 A1 Sep. 2, 2004

(51) Int. Cl.
*A61B 1/32* (2006.01)
(52) U.S. Cl. .................................. 600/245
(58) Field of Classification Search ............ 600/199, 600/200, 212, 223, 241, 245, 246, 188, 189, 600/191, 192, 248, 249; 362/572
See application file for complete search history.

(56) References Cited

U.S. PATENT DOCUMENTS

| | | | |
|---|---|---|---|
| 2,296,793 A | 2/1942 | Kirschbaum | |
| 2,840,070 A | 6/1958 | Tofflemire | |
| 3,592,199 A | 7/1971 | Ostensen et al. | |
| 4,052,980 A | 10/1977 | Grams et al. | |
| 4,300,541 A * | 11/1981 | Burgin | 600/213 |
| 4,337,763 A | 7/1982 | Petrassevich | |
| 4,562,832 A | 1/1986 | Wilder et al. | |
| 4,784,150 A | 11/1988 | Voorhies et al. | |
| 5,035,232 A | 7/1991 | Lutze et al. | |
| 5,159,921 A | 11/1992 | Hoover | |
| 5,237,985 A | 8/1993 | Hodgson et al. | |
| 5,348,470 A * | 9/1994 | McGowan et al. | 433/30 |
| 5,353,786 A | 10/1994 | Wilk | |
| 5,431,153 A | 7/1995 | Lee | |
| 5,520,611 A | 5/1996 | Rao et al. | |
| 5,697,891 A * | 12/1997 | Hori | 600/245 |
| 5,755,660 A * | 5/1998 | Tyagi | 600/205 |
| 5,785,648 A | 7/1998 | Min | |
| 5,928,139 A | 7/1999 | Koros et al. | |
| 5,928,140 A | 7/1999 | Hardten | |
| 5,967,971 A | 10/1999 | Bolser | |

(Continued)

FOREIGN PATENT DOCUMENTS

DE 29713569 12/1997

OTHER PUBLICATIONS

Office Action mailed Jul. 18, 2007 in related CIP U.S. Appl. No. 11/042,496.

(Continued)

*Primary Examiner*—Eduardo C. Robert
*Assistant Examiner*—Michael J Araj
(74) *Attorney, Agent, or Firm*—Baker & Daniels LLP

(57) ABSTRACT

An apparatus includes a surgical retractor and a light conduit releasably coupled to the surgical retractor. In an alternative embodiment, a method of illuminating a surgical cavity includes expanding the cavity with a plurality of surgical retractors, transmitting light from a remote source the to the cavity through a light conduit of at least one of the retractors, focusing a first amount of the light into a first portion of the cavity via the retractor including the conduit, and dispersing a second amount of the light into a second portion of the cavity via substantially lustrous surfaces of the retractors.

6 Claims, 5 Drawing Sheets

U.S. PATENT DOCUMENTS

| | | |
|---|---|---|
| 6,080,105 A | 6/2000 | Spears |
| 6,139,493 A | 10/2000 | Koros et al. |
| 6,193,651 B1 | 2/2001 | DeFonzo |
| 6,196,968 B1 | 3/2001 | Rydin et al. |
| 6,210,325 B1 | 4/2001 | Bartie et al. |
| 6,322,499 B1 | 11/2001 | Evans et al. |
| 6,428,473 B1 | 8/2002 | Leonard et al. |
| 6,895,164 B2 | 5/2005 | Saccomanno |
| 2003/0095781 A1 | 5/2003 | Williams et al. |
| 2004/0172105 A1 | 9/2004 | Vankoski |
| 2005/0165283 A1* | 7/2005 | Hestad et al. ............... 600/212 |
| 2005/0182301 A1* | 8/2005 | Acker et al. ............... 600/204 |

OTHER PUBLICATIONS

European search report mailed Apr. 20, 2006.

\* cited by examiner

LIT RETRACTOR

FIELD OF THE INVENTION

The present invention relates generally to the field of medicine, and, more particularly, to illuminated surgical retractors.

BACKGROUND

In general, surgical retractors are used to push, pull, hold and/or fold skin, flesh and/or other tissue away from a site where a surgical operation or other intervention is being performed. Retractors expand the cavity or working area around the site, providing more room in which to maneuver operating and diagnostic tools. Retractors have also been used to facilitate separation of various tissues from architectures proximal to the surgical site, thereby improving access to and visibility of the site.

Historically, surgical retractors have been comprised of two main parts: a body or handle portion and an insertion portion or insert. The body is typically held by an operator when manipulating the retractor or coupled to a support frame that may include weights or mechanisms designed to facilitate desired movements and hold the retractor in place. The insert is suitably configured to move or grasp the desired tissues. For example, by putting a hook-shaped insert into a surgical cavity and then rotating it, surrounding tissues may be snared and then pulled away from the working environment. Not surprisingly, a single size and shape for retractors has not been practical. Indeed, a wide variety of geometries has been developed for different surgical procedures. Retractors have also been used in conjunction with external lighting systems wherein the retractor holds the body tissue out of the way while the lighting system concurrently illuminates the body cavity. However, relying on directed lighting external to a surgical cavity can be problematic due to difficulties in projecting the light in the required direction and shadows that may be cast onto the operating field. Moreover, separate retracting and lighting systems may be frustrating for an operator who is forced to manipulate both systems simultaneously, and various problems may arise as separate lighting and retracting tools get in the way of each other and cross paths with other equipment in the operating room.

Some retractor designs have sought to integrate retracting and lighting functions into a single device. However, the various complex ways of housing light sources and delivering light to the inserts in many of these illuminated or lit retractors have produced limited retractor geometries, bulky and/or heavy handles and inserts, and/or maintenance issues. Furthermore, some illuminated retractors have tended to emit narrow spot beams of light directed to rather small locations of the operating site. As such an illuminated retractor is moved, as is typically necessary to perform its very retracting function, the narrow spot beam of light is concurrently (and undesirably) moved around the cavity in various directions. While some other illuminated retractors have been designed to provide more diffuse lighting, historical diffusion techniques such as frost or ground lenses can produce light losses that reduce the overall intensity or brightness (relative to the light source) of any light that is eventually delivered to the cavity. Moreover, depending on the application, sometimes the availability of a directed beam may be desirable.

Consequently, the competing needs for variety in size and geometry, directed lighting and diffuse lighting, and simplicity have tended to limit the effectiveness of historical illuminated retractors.

SUMMARY OF THE INVENTION

The present invention provides an apparatus including a surgical retractor and a light conduit releasably coupled to the surgical retractor.

In an alternative embodiment, the present invention provides an apparatus for illuminated retraction of a surgical cavity. The apparatus includes a means for retracting the surgical cavity, and a means, releasably coupled to the retracting means, for transmitting light into the surgical cavity.

In another alternative embodiment, the present invention provides a method of illuminating a surgical cavity. The method includes expanding the cavity with a plurality of surgical retractors, transmitting light from a remote source the to the cavity through a light conduit of at least one of the retractors, focusing a first amount of the light into a first portion of the cavity via the retractor including the conduit, and dispersing a second amount of the light into a second portion of the cavity via substantially lustrous surfaces of the retractors. The above-noted features and advantages of the present invention, as well as additional features and advantages, will be readily apparent to those skilled in the art upon reference to the following detailed description and the accompanying drawings.

DETAILED DESCRIPTION OF EXEMPLARY EMBODIMENT(S)

It is noted that as used throughout this disclosure and the claims, the terms "finger-releasable," "finger-releasably," and the like mean separable by a human hand(s), finger(s), and/or thumb(s)—without tools; whereas, the terms "releasable," "releasably," and the like mean separable with or without tools.

Figure 1:
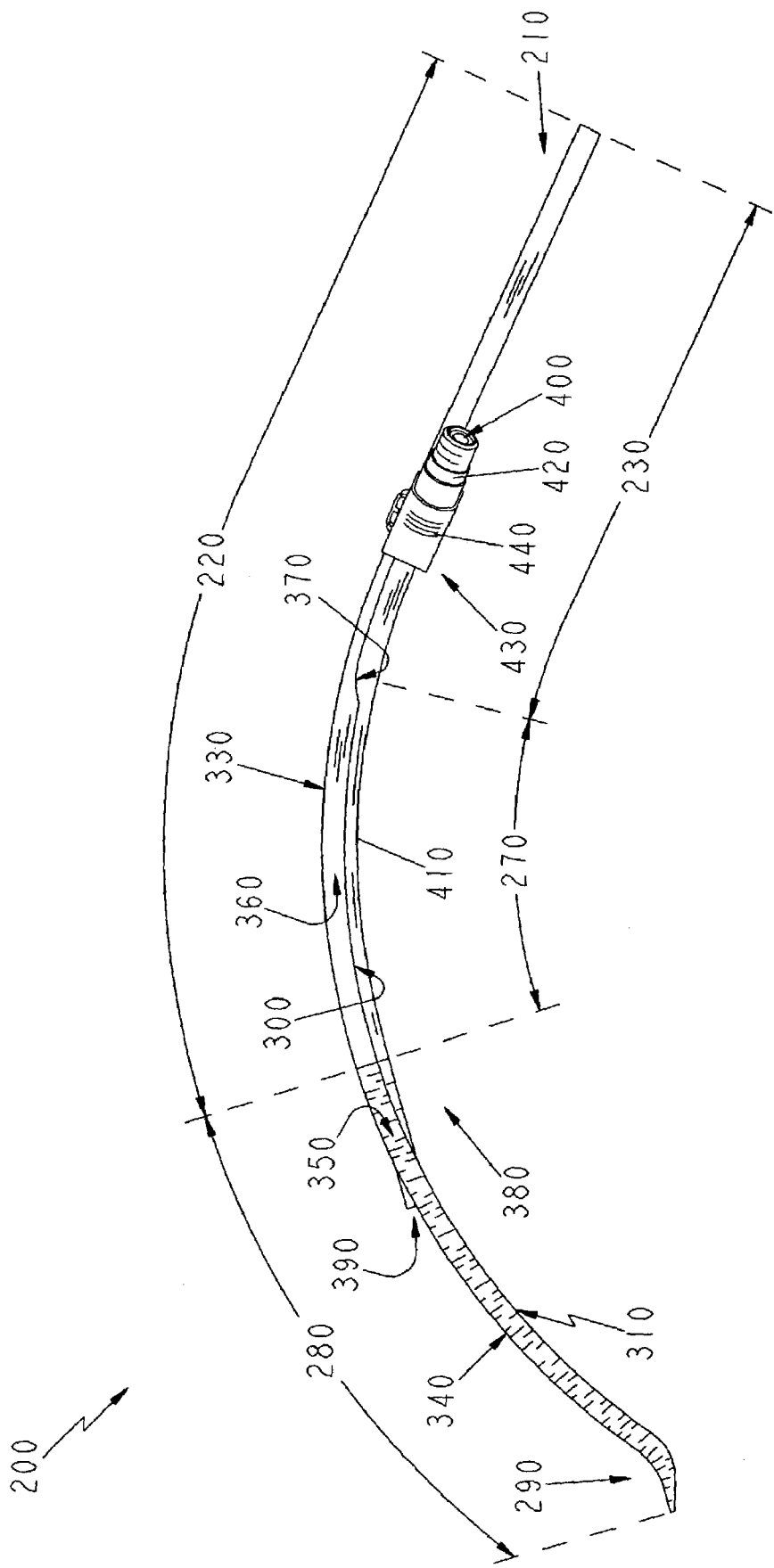
FIG. 1 shows a side (or profile) view of an exemplary apparatus according to the present invention.

FIG. 1 shows a side (or profile) view of an exemplary apparatus 200 according to the present invention. Apparatus 200 is of suitable size and weight for manipulation by hand and includes a surgical retractor 210 that is suitable for sterilization in an autoclave. In the exemplary embodiment, surgical retractor 210 is made from stainless steel. In alternative embodiments, surgical retractor 210 may be made from high temperature plastic or any other material or combination of materials suitable for use in surgical procedures. Surgical retractor 210 includes a body portion 220. Portion 220 includes a generally planar portion 230 defining an aperture or hole 240, an aperture or hole 250, and an aperture or hole 260 (see FIG. 2, FIG. 3, and FIG. 5), and further includes a generally arcuate or curved portion 270 extending from portion 230. Surgical retractor 210 further includes a generally arcuate or curved insertion portion 280 extending from portion 270. Portion 280 includes a generally arcuate or curved end portion 290. Portion 220 includes a lackluster bottom surface 300 and portion 280 includes a lustrous bottom surface 310 (see also FIG. 4. and FIG. 5). Also, portion 220 includes a lackluster top surface 330, while portion 280 includes a lustrous top surface 340. Portion 280 also includes a lustrous side surface 350 extending between surface 310 and surface 340, and further includes an opposing lustrous side surface (not shown). Meanwhile, portion 220 also includes a lackluster side surface 360 extending between surface 300 and surface 330, and further includes an opposing lackluster side surface (not shown). In the exemplary embodiment, the lustrous surfaces (e.g., 340, 350, 310) are produced by suitably color buffing portion 280 in a known manner and the lackluster surfaces (e.g., 330, 360, 300) are produced by suitably mass finishing portion 220 in a known manner. Additionally, portion 280 defines a generally ovular aperture or hole 364 extending between surface 310 and surface 340 (see FIG. 3 and FIG. 5). Surface 300, surface 310, and surface 360 define a groove or channel 370 extending between surface 360 and hole 364 (see FIG. 5), while surface 340 defines a groove or channel 374 that also communicates with hole 364 (see FIG. 2).

Apparatus 200 also includes a light conduit 380 having a side-view geometry or profile substantially conforming to that of surgical retractor 210. Conduit 380 includes an end 390, an end 400, and a casing or sheath 410. Sheath 410 extends through channel 370 and hole 364 such that end 390 protrudes from an intermediate portion of channel 374 (see also FIG. 2, FIG. 4, and FIG. 5). Further, sheath 410 includes a lustrous outer surface 416 extending from end 390 and a lackluster outer surface 418 extending from surface 416 to end 400 (see FIG. 3, FIG. 4, and FIG. 5).

In general, conduit 380 is suitable for use in surgical procedures and configured to transmit externally generated light from end 400 to end 390. Accordingly, conduit 380 includes one or more fiber optic cables and/or any other suitable light transmitting materials housed in sheath 410, and further includes a coupling member 420 fixedly housing a portion of sheath 410 proximal to end 400. Member 420 is configured in a known manner for finger-releasably coupling conduit 380 to an external light source.

In the exemplary embodiment, conduit 380 is reusable and suitable for sterilization in an autoclave. Accordingly, sheath 410 is a rigid stainless steel pipe with lustrous outer surface 416 produced by suitable color buffing and lackluster outer surface 418 produced by suitable mass finishing. In alternative embodiments, the various components of conduit 380 may be made from high temperature plastic and/or any other material or combination of materials suitable for use in surgical procedures and sterilization in an autoclave, and sheath 410 may or may not be flexible. It is noted, however, that in some alternative embodiments conduit 380 may be disposable and, accordingly, in such alternative embodiments all of the components of conduit 380 may be made of relatively inexpensive low temperature acrylics or polymers.

Apparatus 200 further includes a bracket 430 that finger-releasably couples conduit 380 to surgical retractor 210. Bracket 430 includes a sleeve portion 440 fixedly housing a portion of sheath 410 of conduit 380 proximal to end 400 and distal to end 390 (see also FIG. 2 and FIG. 3). Bracket 430 further includes a generally planar flange portion 450 extending laterally underneath portion 230 of surgical retractor 210 proximal to surface 300 (see FIG. 3, FIG. 4, and FIG. 5). Bracket 430 also includes a button or peg 460, having a plurality of slits 470 therein, extending upward from flange portion 450 and snugly fitted into hole 260 of surgical retractor 210 such that peg 460 (and thus bracket 430 and conduit 380) is finger-releasably coupled to surgical retractor 210 (see FIG. 2 and FIG. 3). It should be appreciated, however, that various components in alternative embodiments may include a screw/socket arrangement, a lever operated latch, or any other suitable alternative coupling or couplings for releasably coupling conduit 380 to surgical retractor 210, including (in some embodiments) a coupling that releasably couples conduit 380 to surgical retractor 210 but does not finger-releasably couple conduit 380 to surgical retractor 210.

Figure 2:
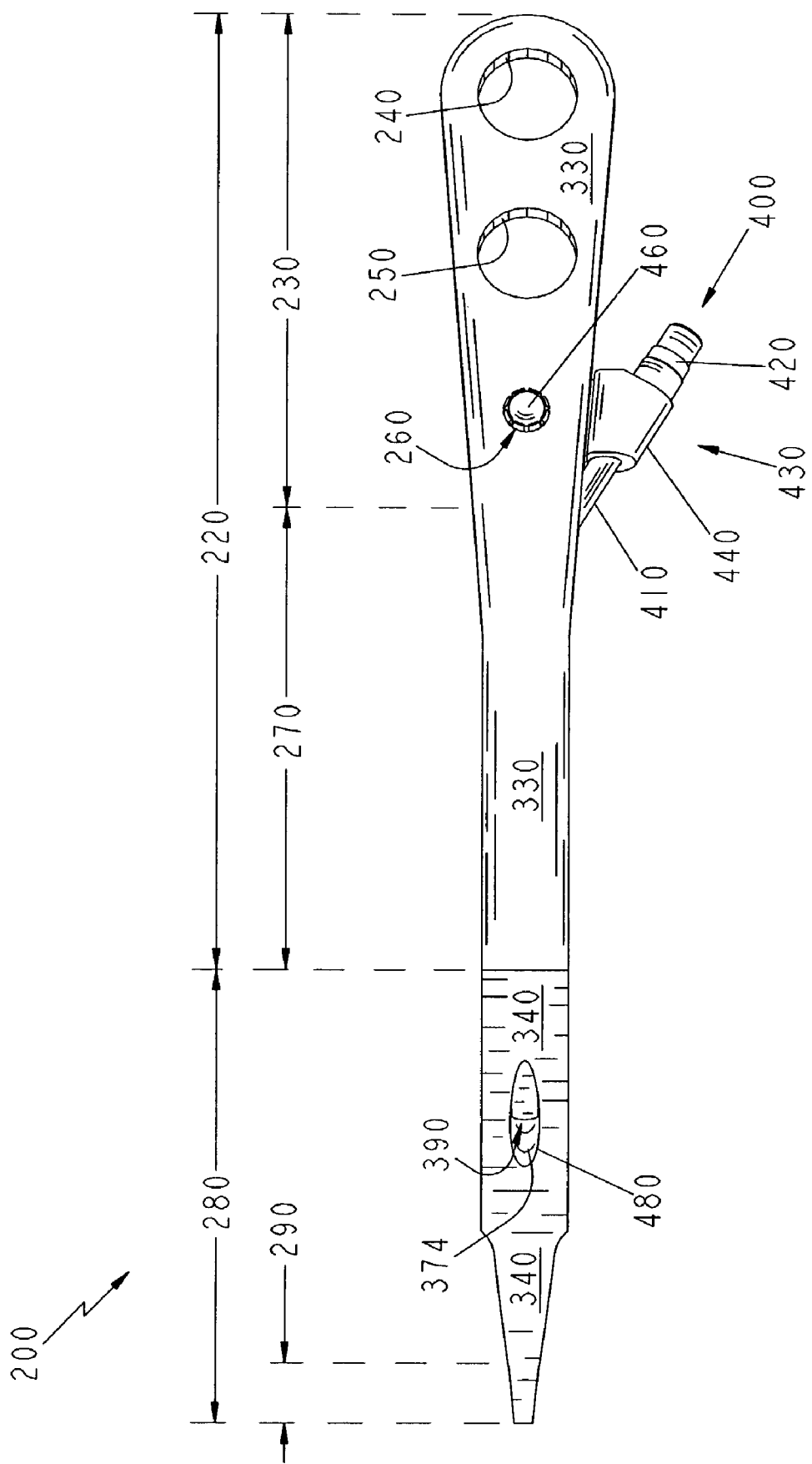
FIG. 2 shows a top view of the exemplary apparatus.

FIG. 2 shows a top view of exemplary apparatus 200. Hole 240, hole 250, hole 260, and channel 374 are discernible in FIG. 2. Additionally, FIG. 2 shows that channel 374 includes a generally ovular rim 480. Portion 220, portion 230, portion 270, portion 280, portion 290, surface 330, surface 340, end 390, end 400, sheath 410, member 420, bracket 430, portion 440, and peg 460 are discussed above in connection with FIG. 1.

Figure 3:
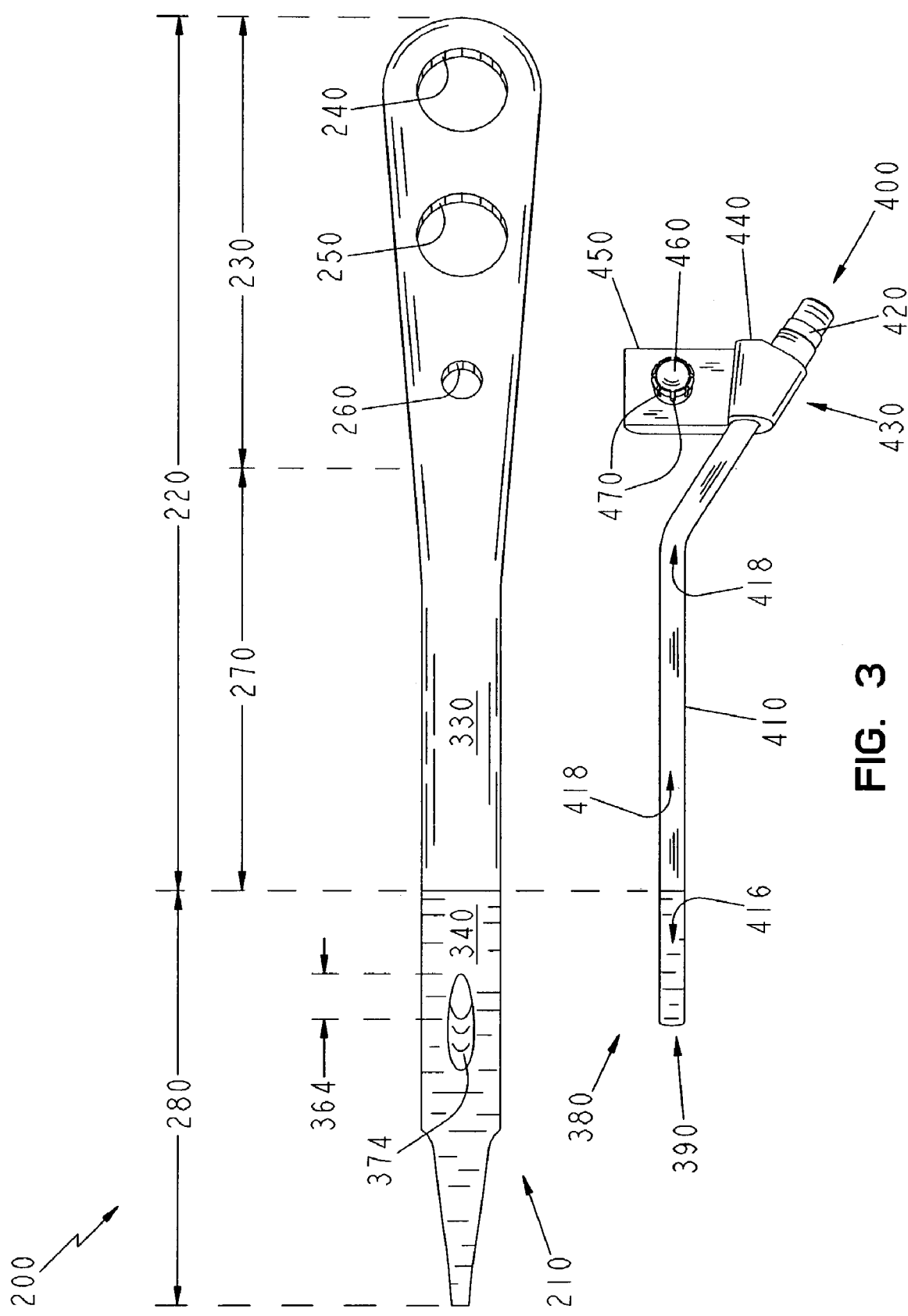
FIG. 3 shows a laterally exploded top view of the exemplary apparatus.

FIG. 3 shows a laterally exploded top view of exemplary apparatus 200. Among other things, surgical retractor 210 (including portion 220, portion 230, hole 240, hole 250, hole 260, portion 270, portion 280, surface 330, surface 340, hole 364, and channel 374), conduit 380 (including end 390, end 400, sheath 410, surface 416, surface 418, and member 420), and bracket 430 (including portion 440, portion 450, peg 460, and slits 470)—all discussed above in connection with FIG. 1—are discernable in FIG. 3.

Figure 4:
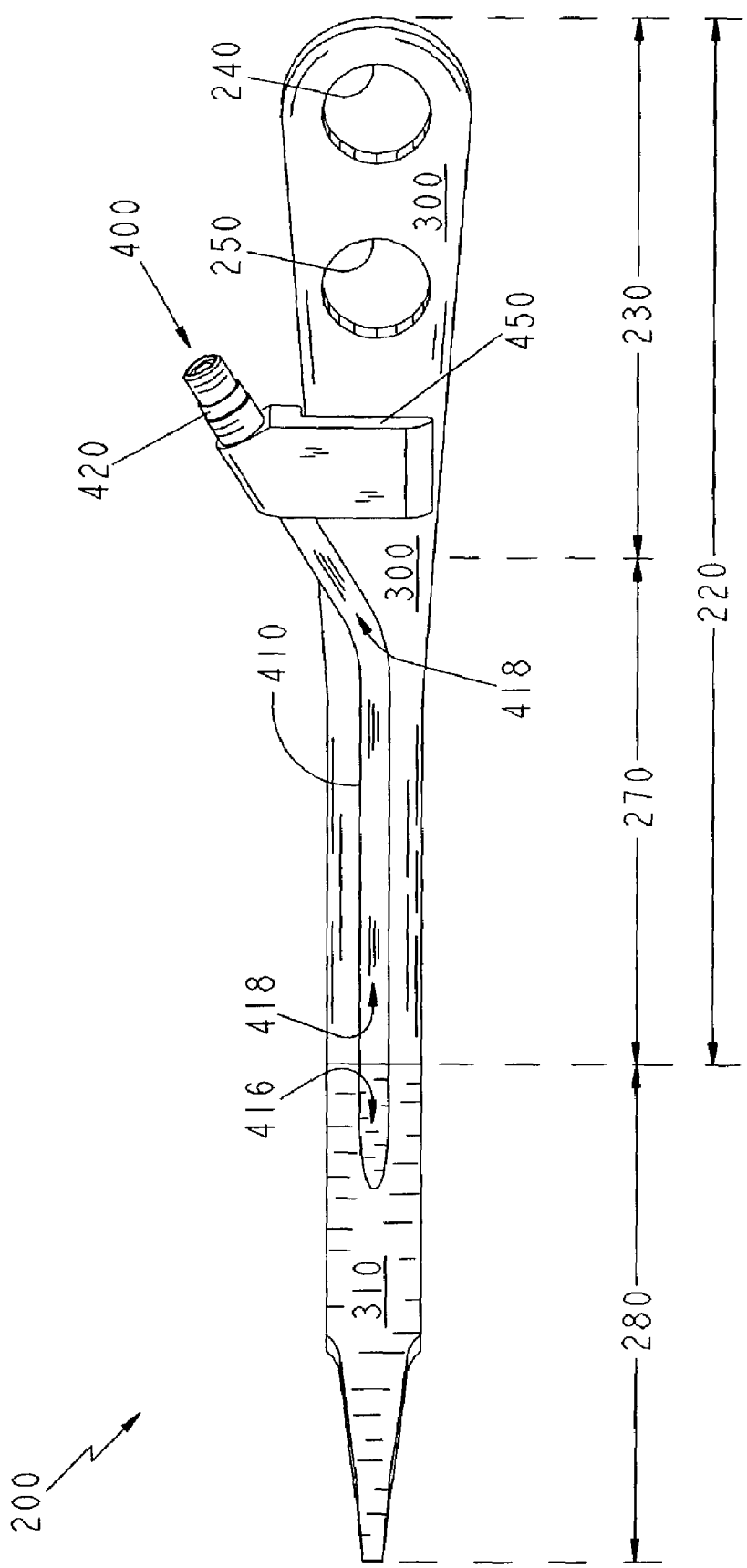
FIG. 4 shows a bottom view of the exemplary apparatus.

FIG. 4 shows a bottom view of exemplary apparatus 200. Among other things, portion 220, portion 230, portion 270, portion 280, hole 240, hole, 250, surface 300, surface 310, end 400, sheath 410, surface 416, surface 418, and member 420—all discussed above in connection with FIG. 1—are discernable in FIG. 4.

Figure 5:
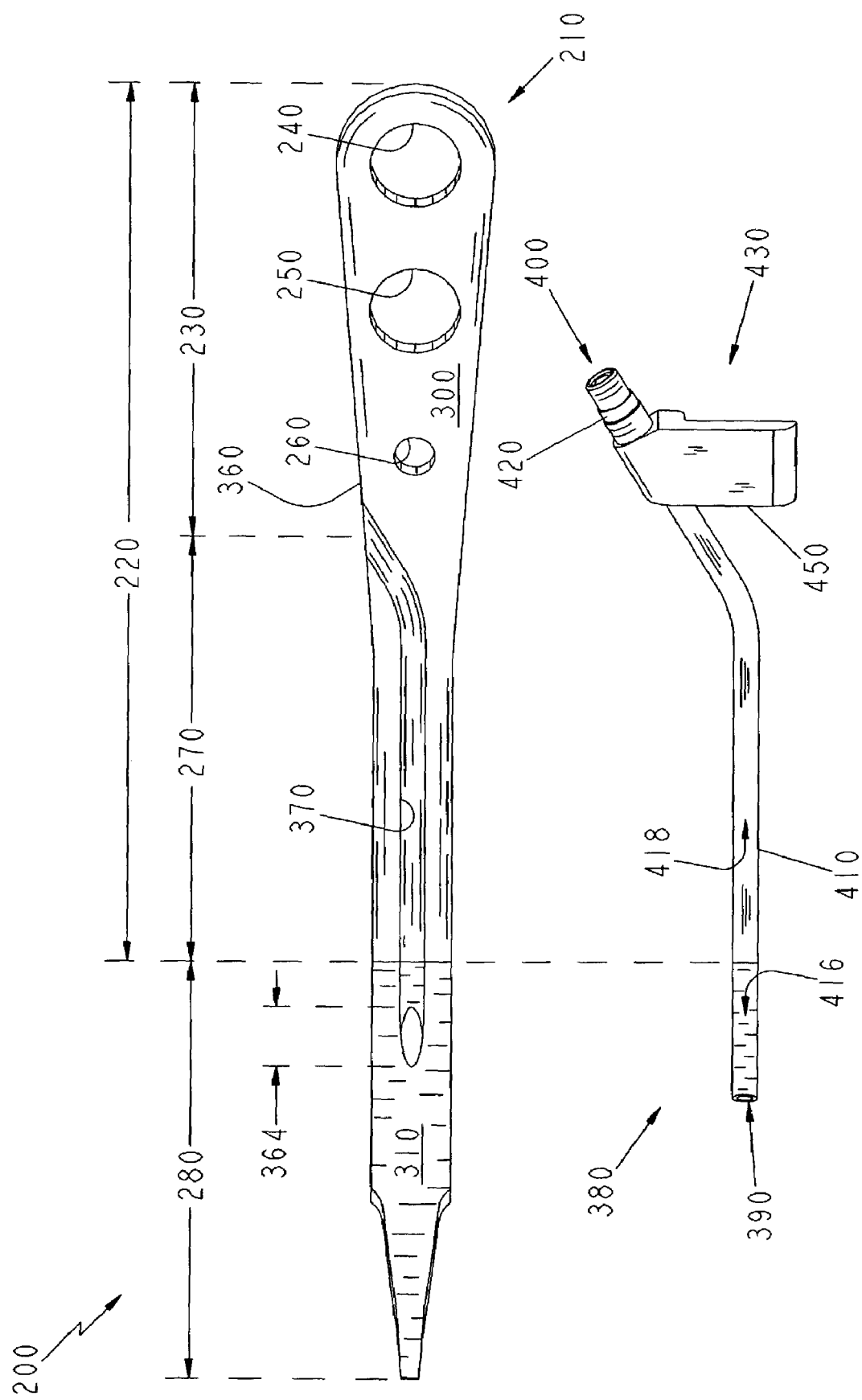
FIG. 5 shows a laterally exploded bottom view of the exemplary apparatus.

FIG. 5 shows a laterally exploded bottom view of exemplary apparatus 200. Among other things, surgical retractor 210 (including portion 220, portion 230, hole 240, hole 250, hole 260, portion 270, portion 280, surface 300, surface 310, surface 360, hole 364, and channel 370), conduit 380 (including end 390, end 400, sheath 410, surface 416, surface 418, and member 420), and bracket 430 (including portion 450)—all discussed above in connection with FIG. 1—are discernable in FIG. 5.

In operation of exemplary apparatus 200, member 420 of light conduit 380 is coupled to a suitable external light source and insertion portion 280 of surgical retractor 210 is inserted into a surgical cavity. Body portion 220 is used to grasp and manipulate surgical retractor 210 as desired. It should be appreciated that the low profile and light weight of exemplary apparatus 200 facilitates its manipulation. In any event, light from the external source is emitted from end 390 of light conduit 380. Channel 374 focuses some of this light into somewhat of a spotlight like beam. Insertion portion 280 is suitably maneuvered to direct the focused light into a desired portion of the surgical cavity. Meanwhile, one or more of the lustrous surfaces (e.g., 340, 350, 310) also reflect a portion of the light present in the surgical cavity, thereby dispersing some of the light to generally illuminate another portion or portions of the surgical cavity at a somewhat lower intensity than the area illuminated by the focused light. Consequently, general or somewhat diffuse lighting of the surgical cavity is provided concurrently with more focused lighting of relatively higher intensity.

For additional dispersion and/or additional focused lighting, additional surgical retractor 210 and/or apparatus 200 are inserted into the surgical cavity as desired. In such cases, various lustrous surfaces of the various surgical retractor 210 may cooperate somewhat to reflect light amongst themselves, thereby enhancing the dispersive effect while maintaining the availability of one or more directable beams.

To facilitate cleaning of apparatus 200 or use of surgical retractor 210 without light conduit 380, conduit 380 is released from surgical retractor 210 by pushing peg 460 of bracket 430 out of hole 260 of surgical retractor 210 with a finger or thumb, and conduit 380 is removed from channel 370 and channel 374 by moving bracket 430 generally down and away from surgical retractor 210 and by pulling bracket 430 generally away from hole 364 such that end 390 of conduit 380 is withdrawn from channel 374 through hole 364, thereby separating conduit 380 and bracket 430 from surgical retractor 210.

The foregoing description of the invention is illustrative only, and is not intended to limit the scope of the invention to the precise terms set forth. Further, although the invention has been described in detail with reference to certain illustrative embodiments, variations and modifications exist within the scope and spirit of the invention as described and defined in the following claims.

What is claimed is:

1. A method of illuminating a surgical cavity, the cavity including a first portion and a second portion, the method comprising the steps of:
    providing a plurality of retractors each having a first portion including a lustrous surface and a second portion including a lackluster surface, wherein each said retractor comprises a curved body, said retractor including a recess, said retractor further comprising:
        a first retractor portion having a substantially lustrous surface including a buffed metal surface; and
        a second retractor portion having a substantially lackluster surface including a mass finished metal surface;
    inserting the first portion of each retractor into the surgical cavity;
    expanding the cavity with the retractors;
    transmitting light into the cavity via a light emitting portion of at least one of the retractors;
    focusing a first amount of light into the first portion of the cavity via the light emitting portion; and
    dispersing a second amount of light into the second portion of the cavity via the substantially lustrous surfaces of the retractors, wherein said light emitting portion of said retractor comprises a light conduit, said light conduit including a projection releasably engaged with said recess of said retractor, whereby said light conduit is releasably coupled to said retractor.

2. The method of claim 1, wherein said light conduit comprises:
    a first conduit portion having a substantially lustrous surface protruding from said surgical retractor and having a buffed metal surface; and
    a second conduit portion having a substantially lackluster surface including a mass finished metal surface.

3. An apparatus for illuminating a surgical cavity, comprising:
    a curved surgical retractor, said surgical retractor including a recess, said surgical retractor comprising:
        a first retractor portion having a substantially lustrous surface including a buffed metal surface; and
        a second retractor portion having a substantially lackluster surface including a mass finished metal surface;
    a light conduit releasably coupled to said surgical retractor, said light conduit comprising:
        a first conduit portion having a substantially lustrous surface protruding from said surgical retractor and having a buffed metal surface; and
        a second conduit portion having a substantially lackluster surface including a mass finished metal surface; and
    a light source associated with said light conduit;
    wherein said light conduit includes a projection releasably engaged with said recess in said surgical retractor.

4. The apparatus of claim 3, wherein said light conduit comprises a rigid tubular structure and said surgical retractor comprises a channel extending substantially lengthwise along said surgical retractor, said rigid tubular structure at least partially positioned in said channel.

5. The apparatus of claim 4, wherein said channel includes a generally ovular rim.

6. The apparatus of claim 3, wherein said light source comprises a fiber optic light source extending through said light conduit.

* * * * *